United States Patent [19]

Fulton et al.

[11] Patent Number: 4,970,300

[45] Date of Patent: Nov. 13, 1990

[54] MODIFIED FACTOR VIII

[75] Inventors: Anne J. Fulton; Alan J. Johnson, both of New York, N.Y.

[73] Assignee: New York University, New York, N.Y.

[21] Appl. No.: 298,413

[22] Filed: Jan. 18, 1989

Related U.S. Application Data

[63] Continuation-in-part of Ser. No. 122,372, Nov. 19, 1987, Pat. No. 4,847,362, which is a continuation of Ser. No. 697,267, Feb. 1, 1985, Pat. No. 4,743,680.

[51] Int. Cl.$^5$ .................. A61K 35/14; C08H 1/00; C08L 89/00; C08B 37/02
[52] U.S. Cl. .................. 530/383; 536/112; 525/54.1; 530/322; 530/362; 530/363; 530/395
[58] Field of Search .................. 536/112; 525/54.1; 530/383, 322, 362, 363, 395; 514/8

[56] References Cited

U.S. PATENT DOCUMENTS

| | | | |
|---|---|---|---|
| 4,229,537 | 10/1980 | Hodgins et al. | 435/177 |
| 4,446,316 | 5/1984 | Chazov et al. | 536/112 |
| 4,496,689 | 1/1985 | Mitra | 525/54.1 |
| 4,698,387 | 10/1987 | Schmidt et al. | 525/54.1 |

OTHER PUBLICATIONS

Finlay, T. H. et al., Anal. Biochem., 87:77, 1978.
Beauchamp, C. O. et al., Anal. Biochem., 131:25-33, 1983.
Bonneaux, F. et al., Experimentia, 37:884-886, 1981.
Hoyer, L. W., Blood, 58:1-13, 1981.
Over et al., J. Clin. Invest., 62:223-234, 1978.
Strauss, H. S., N. Engl. J. Med., 281:866, 1969.
Abuchowski, A. et al., J. Biol. Chem., 252:3578-3581, 1977.
Wood, W. I. et al., Nature, 312:330-337, 1984.
Vehar, G. A. et al., Nature, 312:337-342.
Toole, J. J. et al., Nature, 312:342-347, 1984.
Rotblatt, T. et al., Thromb. Haemost., 50:108, 1983.
Weiss, H. J. et al., Science, 182:1149-1151, 1973.
Fulcher, C. A. et al., J. Clin. Invest., 76:117-124, 1985.
Eaton et al., Biochemistry, 25:505-512, 1986.
Gitschier, J. et al., Nature, 312:326-330, 1984.

Primary Examiner—John Kight, III
Assistant Examiner—G. S. Kishore
Attorney, Agent, or Firm—Darby & Darby

[57] ABSTRACT

Disclosed are conjugates of a protein having antihemophilic factor (Factor VIII) activity linked to nonantigenic ligands. The conjugates have longer half life than the unconjugated protein but maintain substantial Factor VIII activity.

10 Claims, 3 Drawing Sheets

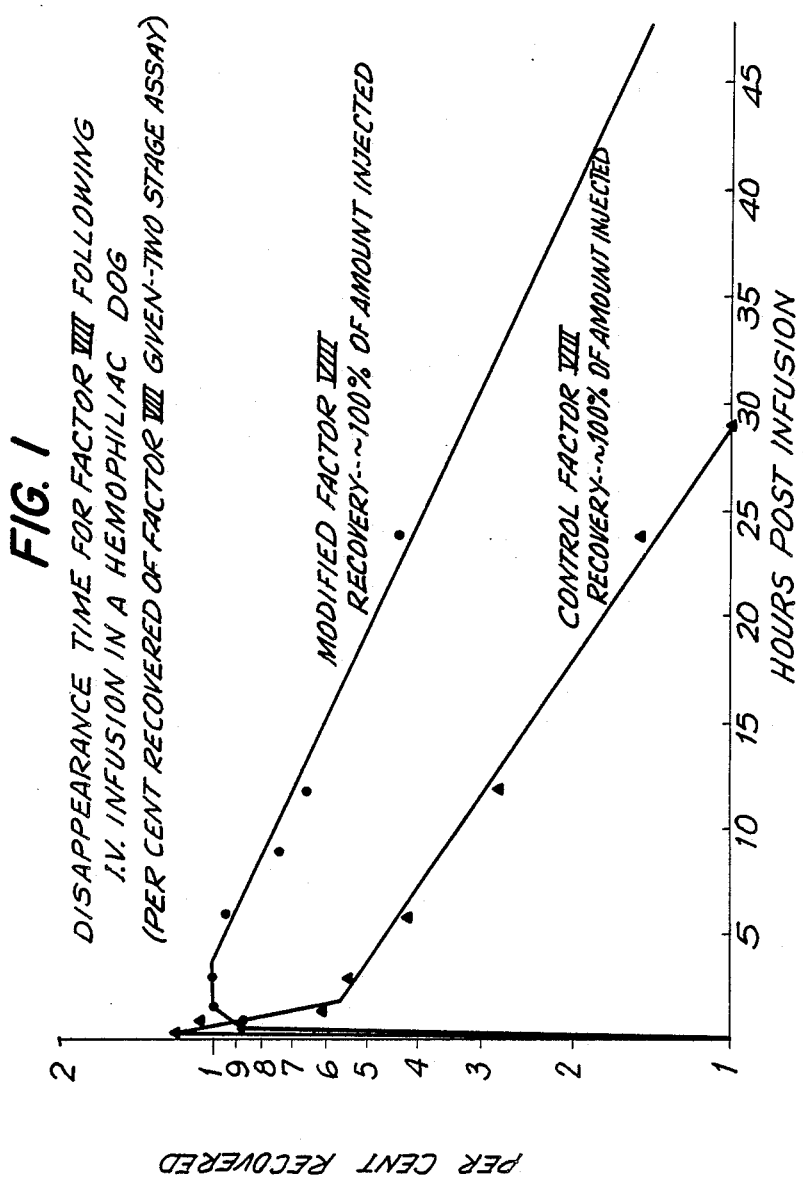

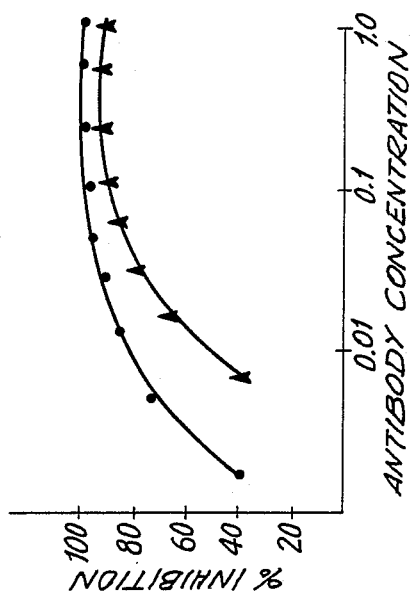
FIG. 2A
FIG. 2B
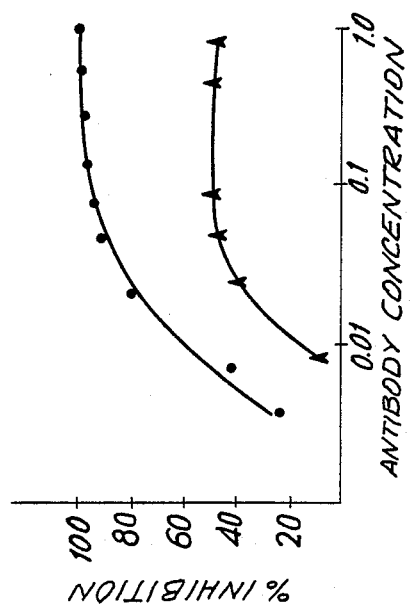
FIG. 2C
FIG. 2D

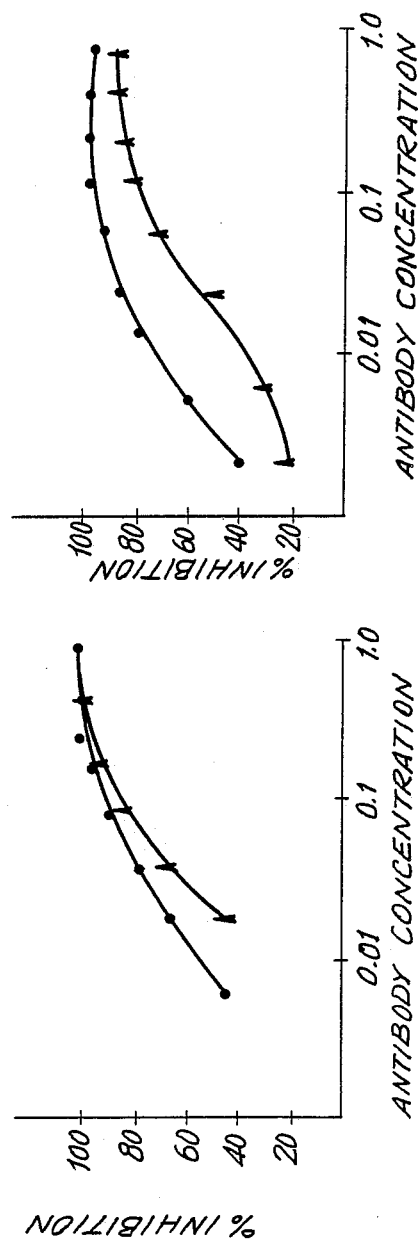
FIG. 2F
FIG. 2E
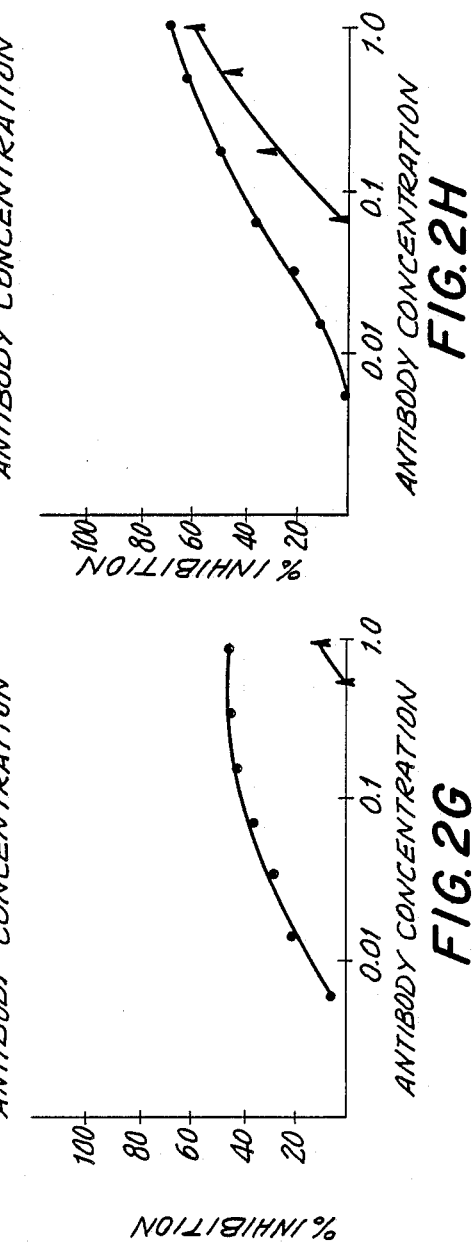
FIG. 2H
FIG. 2G

MODIFIED FACTOR VIII

This application is a continuation-in-part of application S.N. 122,372 filed on Nov. 19, 1987, now U.S. Pat. No. 4,847,362 illued on July 11, 1989, in turn a continuation of S.N. 697,267 filed on Feb. 1, 1985, now U.S. Pat. No. 4,743,680 issued on May 10, 1988.

FIELD OF THE INVENTION

This invention relates to conjugates of a protein having antihemophilic factor (Factor VIII) activity covalently linked to a nonantigenic ligand. This invention also relates to a method for using such conjugates.

Because of historical difficulties in ascertaining the nature and function of Factor VIII, a clarification of what is meant by this term is desirable. Therefore, as used herein, the term "Factor VIII" will denote a procoagulant glycoprotein, the antihemophilic factor, which is further identified as:
  A. Factor VIII Activity (VIII:C), i.e. the functional property of normal plasma, absent in the plasma of patients with severe classic hemophilia, that is measured in standard coagulation assays; and
  B. Factor VIII Antigen (VIII:Ag). i.e. antigenic determinants on Factor VIII measured by immunoassays carried out with human antibodies.

The above definition corresponds to the standard definition for Factor VIII recommended by the International Committee on Thrombosis and Haemostasis (Marder, V.J., et al, *Thromb. Haemost.*, 54:871-872, 1985).

As used herein, the term "protein having Factor VIII activity" will denote individually or collectively native human, porcine or other mammalian Factor VIII and/or fragments of these proteins displaying Factor VIII activity and/or such proteins and/or active fragments thereof produced by recombinant techniques.

BACKGROUND OF THE INVENTION

The process of blood clotting begins with injury to a blood vessel. The damaged vessel wall initiates hemostasis by causing adherence and accumulation of platelets at the point of a vascular injury and by activating the plasma proteins which initiate the coagulation process. Sequential activation via specific proteolytic cleavages and conformational changes of a series of proteins (including Factor VIII) that comprise the coagulation cascade eventually leads to deposition of insoluble fibrin which, together with aggregated platelets, curtails the escape of blood through the point of injury in the damaged vessel wall. Specifically, Factor VIII is activated by thrombin which effects a proteolytic modification (cleavage) on the structure of Factor VIII (Weiss, H.J., et al, *Science*, 182:1149-51, 1973; Hoyer, L., Ch. 4, *Hemostasis and Thrombosis*, 2d Ed., Colman, R.W., Ed., J. B. Lipincott & Co., Philadelphia, USA, 1987; Fulcher et al, *J. Clin. Invest.*, 6:117-24, 1985; and Eaton, et al, *Biochemistry*, 25:505-512, 1986).

Following the initial increase in activity after exposure of Factor VIII to thrombin, there is a decay in activity to below baseline levels. This decay in activity is attributed to further proteolytic cleavage of activated FVIII by thrombin; (and during pathological states) inactivation by thrombin-activated protein C. The activation and inactivation of Factor VIII by thrombin and protein C allows a fine measure of control over coagulant activity in vivo. Unfortunately, it may also cause premature denaturation of Factor VIII prior to administration to mammalian hosts in need of such treatment.

The primary source of native Factor VIII is plasma. In addition, recombinant Factor VIII has recently become available through the cloning of the Factor VIII gene (Gitschier, J., et al, *Nature*, 312:326-330, 1984; Wood, W.I., et al, *Nature*, 312:330-337, 1984; and Vehar, G.A., et al, *Nature*, 312:337-342, 1984 and Toole, J.J., et al, *Nature* 312:342, 1984).

Recently, several groups of investigators have purified Factor VIII with specific activities as high as 3000 units per milligram (Rotblatt, F., et al, *Thromb. Haemost.*, 50:108, 1983; Fulcher, C.A., et al, *J. Clin. Invest.*, 76:117-124, 1985; Johnson, A.J., et al, *Scripps Clinic and Research Foundation and the NHLBI*, 1982).

The Factor VIII in all of the concentrates available to date (regardless of their purity) has an in vivo half-life of about 8-12 hours (Hoyer, L.W., *Blood*, 58:1-13, 1981) necessitating multiple infusions of concentrate for the maintenance of hemostasis. The level of Factor VIII antigen in plasma falls off at the same rate as the clotting activity, which suggests that Factor VIII is rapidly removed from the circulation and that the decline in Factor VIII activity is not simply or even primarily due to its inactivation.

The lower curve in FIG. 1 (which is a plot of the log of Factor VIII activity vs. time) shows a typical pattern of Factor VIII elimination from the bloodstream of a hemophilic dog. This pattern is similar to the one occurring in man. Phase 1 of the disappearance time curve is shown by the sharp nonlinear decrease in FVIII activity (to about 55% of the initial value) which follows its administration in vivo. This has been attributed to diffusion into the extravascular space or a more rapid removal of the higher molecular weight forms (Over et al., *J. Clin. Invest.* 62:223-234, 1978). Phase 2 of the disappearance time curve in FIG. 1, from which the half-life is determined, is demonstrated by the subsequent substantially linear decrease in activity. This second gradual decrease in activity has been attributed to clearance by the reticuloendothelial system and possibly protein C inactivation.

In this application, the term "disappearance time" or "clearance time" will be used to denote the time taken for FVIII activity to decrease to 50% of its maximum level. The maximum occurs in Phase 1 and the decrease to 50% may occur in Phase 1 or Phase 2.

Another problem incurred with infusion of Factor VIII stems from the fact that many recipients develop inhibitors (antibodies) which neutralize the activity of the infused Factor VIII. As many as 14% of the patients receiving Factor VIII infusions develop such inhibitors (Strauss, H.S., *N. Engl. J. Med.* 281:866, 1969). The presence and activity of these inhibitors are sometimes sufficient to eliminate the beneficial effect of Factor VIII infusion.

Attempts to bypass the effects of these inhibitors which include infusion of inhibitor-bypassing agents (e.g., Feiba made by Immuno, Austria and concentrates of Factors II, VII, IX and X) have been only partially successful. The bypassing agents themselves cause undesirable side effects and their mechanism of action is unknown. Immunosuppressive techniques have also been only partially successful usually in patients who have spontaneous anti-FVIII antibodies. However, administration of immunosuppressants raises the risk that the patient will b vulnerable to AIDS and opportunistic infections.

It would therefore be desirable to modify Factor VIII prior to i.v. infusion and thus: (a) prevent or lessen the initial, sharp decrease in Factor VIII activity in Phase 1 (ref. FIG. 1, lower curve) following the infusion of Factor VIII; (b) slow down the rate of the subsequent gradual decrease in Factor VIII activity in Phase 2 (and thereby prolong the Factor VIII half-life); (c) protect the infused Factor VIII from antibody inhibition by decreasing the ability of Factor VIII to bind to existing antibodies; (d) decrease the ability of the infused Factor VIII to generate further antibodies; and (e) modify the Factor VIII under conditions that would not substantially affect its overall sustained ability to participate in the coagulation cascade. The present invention meets one or more of these objectives in whole or in part as further described below.

DESCRIPTION OF THE PRIOR ART

Various proteins, especially enzymes, unrelated to Factor VIII, have been previously coupled to carbohydrates, polyols, other proteins and amino acids for the purpose of increasing their stability, their resistance to proteolysis and heat, and/or decreasing their immunogenicity. For example, alpha- and beta-amylase have each been coupled to dextran (*Arch. Bioch. Bioph.* 167:777–779, 1975). The resulting conjugates displayed increased stability to denaturing conditions and markedly decreased immunogenicity when injected in heterologous hosts.

Abuchowski, A., et al, *J. Biol. Chem.*, 252:3582–3586, 1977 attached methoxypolyethylene glycols (hereafter polyethylene glycols will be abbreviated "PEG" and methoxy polyethylene glycols will be abbreviated "M-PEG") of 1900 and 5000 m.w. to bovine serum albumin and bovine liver catalase (using trichloro-s-triazine as the coupling agent) to decrease the immunogenicity of these proteins. These PEG polymers are nonimmunogenic linear uncharged polyhydric alcohols. The resulting conjugates had markedly decreased immunogenicity, prolonged half-life in vivo, and increased stability in vitro against proteases.

Several general methods have been developed for the covalent attachment of polypeptide ligands to carbohydrate supports notably in conjunction with the development of specific affinity chromatography media. (Cuatrecasas, P., *Advan. Enzymol.*, 36:29, 1972; Finlay, T.H., et al, *Anal. Biochem.*, 87:77, 1978; Hearn, N.W., et al, *J. Chromatogr.*, 185:463, 1979). Some of these methods have also been adapted for activating PEG or carbohydrates in solution, thus making the coupled polymer-protein adducts suitable for intravenous (i.v.) infusion.

For example, cyanogen bromide has been used for coupling dextran to proteins (Marshall, J.J., et al, *Arch. Biochm. Biophys..* 167:777–779, 1975); Trichloro-s-triazine (TST) has been used to activate agarose (for affinity chromatography) (Hodgins, et al, *J. Chromatogr.*, 202:381, 1980) and polyethylene glycols for soluble polymer-protein adducts, (Abuchowski, et al, 1977, supra); 1,1'carboaryldiimidazole (CDI) has been used to activate both agarose (Hearn, supra 1979) and soluble PEG (Beauchamp, C.O., et al, *Anal. Biochem.*, 131:25, 1983); and sodium periodate has been used to create aldehyde groups in dextran molecules which are then coupled to proteins including hemoglobin (Bonneaux, F., et al, *Experientia*, 37:884–886, 1981).

Conjugates constructed using the above methods have been shown to increase the in vivo half-life of specific proteins and/or decrease their antigenicity. Heterologous enzymes (such as asparaginase) have been conjugated in this manner and thus made more suitable for therapeutic use. The half-life of several enzymes was thus increased two- to ten-fold in mice and as much as 30-fold in man. Several of the conjugated enzymes have been shown to display therapeutic activity in vivo. However, neither these enzymes nor albumin are in any way related to Factor VIII in terms of either structure of function. Indeed, Factor VIII is a unique, variable, high-m.w. protein consisting of more than one polypeptide chain; it is only relatively stable and only over a very narrow pH range (about 5.8–7.8); it is easily inactivated by conditions and reagents benign to other proteins; it adsorbs readily to glass and most plastic surfaces; and it is present in plasma in only nanogram amounts. Therefore the previous success in polymer-protein adduct formation is of little predictive value vis-a-vis coupling of Factor VIII and the use of such coupling to accomplish desirable modifications in Factor VIII properties.

SUMMARY OF THE INVENTION

One aspect of the invention relates to an infusible conjugate of a protein having Factor VIII (antihemophilic Factor) activity covalently linked to a nonantigenic ligand, said conjugate retaining at least a substantial portion of the initial Factor VIII activity of said protein, said conjugate being activatable by thrombin and said conjugate having substantially prolonged in vivo disappearance time and substantially decreased immunogenicity and immunoreactivity compared to said protein in the unconjugated state.

A conjugate of Factor VIII and dextran is preferred.

Other aspects of the invention relate to methods for making such conjugates and for treating hemophilia, the latter comprising infusing a mammal in need of such treatment with a procoagulant-activity-restorative effective amount of a conjugate of a protein having antihemophilic factor activity and a nonantigenic ligand, said conjugate being activatable by thrombin and having a substantially decreased antigenicity and immunoreactivity and a substantially increased in vivo disappearance time in the bloodstream of said mammal compared to said protein in the unconjugated state.

BRIEF DESCRIPTION OF THE DRAWINGS

FIG. 1 is a semilog plot of Factor VIII activity in the blood of a hemophilic dog as a function of post-infusion time. The curve connecting the circles corresponds to dextranconjugated Factor VIII whereas the curve connecting the triangles corresponds to unconjugated Factor VIII (control).

FIG. 2 (A–H) are plots of antibody inhibition of Factor VIII activity versus antibody concentration.

DETAILED DESCRIPTION OF THE INVENTION

(A) Purification of Factor VIII

In accordance with the present invention, Factor VIII from a suitable source is first preferably purified. The minimum specific activity that will permit conjugation is about 0.2 units/mg such as cryoprecipitate, but activities greater than 5 units/mg are preferred with further purification possible after conjugation. Activities greater than 25 units/mg are particularly preferred. It is of course desirable to use as pure Factor VIII as possible.

Purification preferably takes place in the presence of protease inhibitors (e.g., heparin, Trasylol, Benzamidine, APMSF and Inhibitor 805) but only because the results can be analyzed with greater accuracy. Use of protease inhibitors is not an essential feature of the present invention. If plasma is used, cryoprecipitate is usually first prepared according to well-known techniques.

One preferred technique for the preparation of cryoprecipitate involves use of fresh-frozen plasma softened at room temperature, crushed and quick-thawed in an inert (e.g. stainless-steel) container placed in a water bath (37° C.) with constant stirring. Plasma temperature is kept below 2° C. during thawing. The plasma is then centrifuged at 3000xg for 30 minutes at 4° C. The supernatant is discarded and the cryoprecipitate is reconstituted into 0.02 M Tris, 0.02 M trisodium citrate, 0.06 M NaCl, pH 7.2 to 1/10 of its original volume. Of course, other well-known methods for obtaining cryoprecipitate may also be used.

If cryoprecipitate or commercial Factor VIII concentrate are used as the source of Factor VIII, a suitable subsequent purification procedure may be selected among those well-known in the art. Various combinations of cryoprecipitation, polyethylene glycol precipitation, and chromatographic techniques (including but not limited to hydrophobic affinity chromatography, immunoaffinity chromatography, ion-exchange chromatography, etc.) may be used according to the starting material (plasma, cryoprecipitate, Factor VIII concentrate, etc.) and according to the purity and yield desired.

The techniques disclosed in Zimmerman, U.S. Pat. No. 4,361,509 and especially in Mathews, U.S. Pat. No. 4,743,680 represent preferred chromatographic purification methods. Another preferred purification protocol is the following:

Cryoprecipitate (or commercial concentrate) is subjected to a first chromatographic purification using a polyelectrolyte E-5 (PE-E5) column (PE-E5 is a copolymer of ethylene and maleic anhydride substituted with 5 mole % dimethylamino propylimide functional groups, Johnson, A.J., et al, *J. Lab. Clin. Med.*, 92:194-210, 1978). Prior to use, PE-E5 is preferably protonated, e.g.: by suspending the resin in 0.15 M NaCl (at a PE/saline ratio of 1/10) and maintaining the pH at 4.0 for 20 minutes by dropwise addition of 0.5 M citric acid. The pH is then adjusted to 6.0 with 0.5N NaOH and packed in an appropriate size column depending on the amount of material to be processed (as is well-known in the art). The PE-E5 resin is then washed with four column volumes of 0.15 M NaCl, 0.02 M citrate, pH 6.6. In the experiments described below, for most preparations, a 300 ml column was used with 3g protein for the first PE chromatography step and a 10 ml column was used with 10 mg protein (excluding albumin) for the second PE chromatography step.

The sample is loaded onto the first PE column at a protein content of 5 mg/ml in 0.15 M NaCl, 0.02 M trisodium citrate, 0.02 M Tris, pH 6.6. A preferred sample size is 40 mg protein/gram of PE-E5. The column is then washed, e.g., with 2 column volumes of 0.15 M NaCl, 0.02 M trisodium citrate (pH 6.6), followed by 10 volumes of 0.35 M NaCl, 0.02 M MES (2-(M-morpholino)ethane sulfonic acid) pH 6 (0.02 M sodium acetate could be used instead of MES). Factor VIII is eluted, e.g., with two volumes of 0.25 M CaCl$_2$, 0.02 M MES (or 0.05 M sodium acetate), 10% glycerol, pH 6.0.

The eluate ("the first eluate") purified according to this procedure had a specific activity of 70-140 units/mg.

When particularly high purity FVIII is desired, the eluate from the first PE-E5 column is subjected to a series of affinity chromatography steps sequentially: a gelatin/agarose column followed by an anti-fibrinogen agarose column, in turn followed by an anti-von Willebrand factor agarose column. All three columns can be equilibrated with the PE-E5 elution buffer containing 0.2% human serum albumin. A suitable flow rate through each column is 25 ml/h. Factor VIII is thus excluded in the effluent from each of these three columns.

The gelatin/agarose column may be prepared as follows: Swine skin gelatin is dissolved in 0.1 M MOPS (3-(N-morpholino) propane sulfonic acid) buffer pH 7.5 at 40° C. to a concentration of 10 mg/ml. Affi-Gel 10, an activated polysaccharide support from Bio-Rad Laboratories, Richmond, Calif. is quickly washed in ice-cold distilled water and equilibrated in the MOPS buffer at room temperature. Affi-Gel is mixed with the gelatin (1:3 v/v) and the coupling reaction is allowed to proceed at 40° C. for several (e.g. 4) hours. The unreacted groups on the gel are then blocked e.g. with 0.1 M ethanolamine for 1 hour prior to extensive washing with coupling buffer. The gel is stored at 4° C. in the same buffer as that used for the PE-E5 elution to which 0.02% sodium azide may be added.

As indicated above, the second and third affinity columns are designed to remove fibrinogen and von Willebrand factor, respectively. Antifibrinogen antibodies may be obtained from Sigma Chemical Co., St. Louis, Mo. or Miles Laboratories, Naperville, Ill.

IgG to von Willebrand factor for the experiments described here were prepared as follows: vW factor was purified by the method of Johnson, A.J., et al, *J. Lab. Clin. Med.*, 92:194-210, 1978 using batch adsorption and elution on PE-E5 and PE-E100, followed by precipitation with PEG. This material was used to immunize three rabbits over a six-week period. All three rabbits produced antibodies to vW factor and the IgG fraction from the rabbit plasma was purified by chromatography on diethylaminoethyl Affi-Gel blue (from Bio-Rad) in accordance with the manufacturer's instructions. Samples were first dialyzed overnight against low ionic strength buffer (0.02 M K$_2$HPO$_4$, pH 8.0) and then processed through an Affi-Gel blue column (5 ml of column/ml of sample) equilibrated in the same buffer. The IgG was collected in the effluent. The peak fractions were pooled and concentrated by dialysis against CARBOWAX 20000 (a polyethylene glycol, m.w. 20,000) followed by equilibrium dialysis in 0.1 M NaCl, 0.05 M MOPS, pH 7.5. IgG was stored frozen at −70° C. IgG containing antibodies to each of these contaminants (fibrinogen and vWf) were bound to Affi-Gel (25mg of protein per ml of Affi-Gel) by mixing in accordance with the manufacturer's instructions.

The final effluent containing Factor VIII from the three affinity columns was then diluted with deionized water to lower the calcium concentration to 0.05 M and subjected to an additional chromaography step on a second PE-E5 column. The Factor VIII was applied to the column and the column was washed with 20 column volumes of 0.35 M NaCl, 0.02 M MES pH 6.0. The factor was eluted with 0.25 M CaCl$_2$, 0.02 M MES, 10% glycerol, pH 6.0. This second PE-E5 eluate had a specific activity of 3000-4000 units/mg (this and all activity measurements were made by two-stage FVIII assay according to Newman, J., et al, *Brit. J. Haematol.*, 21:1-20, 1971). Alternatively, only the first PE-E5 column may be used or the first and second PE-E5 columns may be used and one or all of the intermediate affinity chromatography steps may be omitted.

Another preferred procedure is one according to Mathews U.S. Pat. No. 4,743,680 a modification as described below:

Cryoprecipitate or Factor VIII concentrate is first washed in ice-cold tris buffer (0.02 M tris, pH 7.2). It is then extracted in 4 volumes (w/v) of deionized water containing 0.02 M tris buffer, 0.02 M citrate and 0.06 M NaCl, pH 7.2. It is then absorbed for 20 minutes with 5% aluminum hydroxide $Al_2(OH)_3$ (Superfos) and centrifuged. The following are added under stirring: 5 units/ml heparin; PEG to 1% (or between 0.5 and 5%); 0.1 M acetic acid or HCl to bring the pH to 6.6 (or within the range between 6.2 and 6.7). This is followed by stirring for about 15 minutes. The mixture is centrifuged and sorbitol is added to 1 M. A small "guard" column and a larger chromatography column are prepared in series as follows:

The volume ratio of guard column to main column is 1:20. The purpose of the guard column is to remove traces of procoagulant Factors II, VII, IX and X that might become activated, or traces of activated coagulation factors such as thrombin that might (a) cause premature activation of Factor VIII and (b) decrease the Factor VIII yield obtained by the purification procedure and (c) cause instability of the Factor VIII. The guard column is packed loosely with 1/40th the amount of the same chromatographic support as the main column to absorb the procoagulant factors, preferably quaternary amino methyl Sepharose ("QMA") and an equal amount of carboxymethyl Sepharose to adsorb the thrombin. Both packed columns are soaked with 1 M NaCl in 0.02 M Tris, pH 7.4 and equilibrated with 0.02 M Tris, pH 7.4, 0.165 M NaCl, 1 M sorbitol until the ionic strength of the effluent is equal to that of the equilibrating solution.

The cryoprecipitate is diluted to 4 mg/ml protein content with the equilibration buffer and 0.01 M citrate is added.

The cryoprecipitate is run through the guard column and loaded on the main column. When the total volume of the sample has been run through the guard column, the guard column is disconnected from the main column and the main column is washed with 5 volumes of the equilibrating buffer followed by 2-2.5 column volumes of 0.05 M Tris-acetate pH 6.8, 10% glycerol, 2% ethanol.

The Factor VIII is eluted with 0.5 M Tris-acetate, pH 6.8, 10% glycerol, 2% ethanol and 0.35 M $CaCl_2$. Other suitable washing and elution conditions may also be used as will be apparent to those of ordinary skill in the art. The advantage of using the guard column is demonstrated by prolonged stability of Factor VIII activity on storage.

The purification processes described above were used to obtain sufficiently pure Factor VIII to permit a high conjugation reaction yield and to permit analysis by polyacrylamide gel electrophoresis such that scientifically unassailable conclusions would be drawn regarding the preparation and therapeutic viability of the conjugate in the experiments described below. These purification processes were also used to obtain a pure preparation of Factor VIII suitable for administration to human or other mammalian subjects in need of such treatment, i.e., as free as possible of contaminants and as concentrated and active as possible. However, as stated above, Factor VIII preparations of relatively modest purity (such as 2-5 units/mg) can be used in accordance with the present invention.

It will be understood that the foregoing methods for the purification of Factor VIII are simply preferred procedures and that many other known procedures may be used, including immunoaffinity columns with anti-vWF antibody or anti-Factor VIII antibody, as will be readily appreciated by those of ordinary skill in the art. Instead of quaternary aminomethyl sepharose (which is preferred) another positively charged ionic group (such as aminoethyl, diethylaminoethyl, triethylaminoethyl, poly(ethyleneimine), epichlorohydrin triethanolamine, etc.) can be coupled to a solid support (e.g. sepharose, silica, cellulose or acrylamide) and used as the absorbent in the ion-exchange chromatography step.

The purified Factor VIII is then coupled to a non-antigenic ligand. Conjugation of Factor VIII is intended to produce a Factor VIII preparation having one or more of the following properties: decreased-antigenicity, decreased-immunorecognition, prolonged disappearance-time in vivo and a preparation that continues to be active as a blood coagulant protein and is suitable for administration to mammals in need of treatment.

Acceptable conjugates should have such a combination of procoagulant activity, increased in vivo disappearance time and reduced immunochemical reactivity and immunogenicity properties to provide advantageous alternatives to unconjugated Factor VIII. For example, if a conjugate has 50% of the activity of unconjugated Factor VIII but has a disappearance time that is sufficiently prolonged to compensate for this loss this is already an advantage because it may allow for wider spacing of consecutive infusions with Factor VIII and/or a smaller total number of infusions. It will also be an advantage if the conjugated preparation, due to its decreased antigenicity, will generate substantially fewer inhibitors (e.g. would generate about half the antibodies that neutralize Factor VIII activity when administered intravenously in the course of treatment in the vast majority of hosts compared to unconjugated factor). If, in addition to decreased antigenicity, the conjugate displays a substantially longer clearance time (such that it takes for example at least 50% longer to clear from the host than unconjugated factor), such that after the lapse of time substantially more conjugate is left in the bloodstream of the host than would remain of unconjugated factor, this constitutes an additional advantage permitting less frequent administration of Factor VIII or administration of smaller doses. Even if the conjugate has only about 35% of the activity of the unconjugated factor, use of such a conjugate would still be advantageous, as described above.

Thus, a "substantial portion of the activity" of the unconjugated protein shall mean at least about 35% of the activity of the protein in the unconjugated state.

A "substantially longer" infusion interval shall mean at least about 24 hours under acute bleeding conditions when the norm is 8-12 hours. Under these circumstances, a repeat infusion might not be necessary for most bleeds.

Accordingly, the conjugate should have such initial activity, antigenicity, immunoreactivity and useful life (low disappearance rate and/or prolonged half-life) in the blood stream such that, 12 or more hours after infusion, the bloodstream of the host will still contain a greater amount of the administered Factor VIII activity than it would if unconjugated Factor VIII had been administered.

Chemical Modification Procedures

Dextran (MW of 10, 40 and 70 kD) was oxidized by reaction with sodium periodate according to a modification of the procedure of Jeanes, A., et al, *J. Am. Chem. Soc.* 72:2655, 1950 as follows: a 10% ice-cold dextran solution was mixed with solid sodium periodate to a final concentration of 0.18 M. The reaction mixture was incubated overnight at 4° C. in the dark (to limit the extent of reaction) under constant mixing. Excess periodate was removed by chromatography of the reacted mixture on Sephadex G-25 or by dialysis against several changes of distilled water. The thus oxidized dextran can then be frozen or lyophilized for storage.

Factor VIII (specific activity in excess of 400 u/mg) was then chemically modified by coupling to sodium periodate-oxidized dextrans. (It should be noted that use of highly purified Factor VIII is not necessary.)

The coupling reaction was performed in 0.25 M $CaCl_2$ (or 1.0 M NaCl), 0.02 M MES (or 0.05 M sodium acetate) pH 6.0. Protein concentration was preferably about 0.5 mg/ml. Lyophilized dextran was then added to a final concentration of 10 mg/ml. The reaction was allowed to proceed for 6 hours at room temperature or until Factor VIII activity was reduced to 50–60% of the initial activity as measured by the two-stage assay method of Newman, et al., *Brit. J. Haematol.* 21:1–20, 1971. The reaction was stopped by the addition of 1 M sodium borohydride to a final concentration of 30 mM. A lower concentration is preferred if the protein concentration is also lower. Glucosamine or other neutral amine is added after 30 min incubation with the borohydride to neutralize unreduced aldehyde groups. Samples were stored at −70° C.

The conjugated Factor VIII can be dialyzed or subjected to concentration and diafiltration with a Minitan apparatus (Millipore, Bedford, Mass.) to exchange the high-calcium, sodium borohydride-containing buffer for a physiologic buffer, preferably in the presence of 0.5% human serum albumin.

The coupling of Factor VIII and dextran (of various molecular weights) was verified by several methods such as sodium dodecyl sulfate and borate polyacrylamide gel electrophoresis; Western blotting (using homologous polyclonal anti-Factor VIII antibodies obtained from George King Biomedical Inc., Overland Park, KA); periodic acid silver staining (Dubray, G., et al, *Anal. Biochem.*, 119:325–329, 1982); and sucrose density gradient ultracentrifugation.

The coupling of dextran to Factor VIII does not impair the functional capacity of thrombin-activated Factor VIII to act as a cofactor in the activation of Factor X. Use of dextran with a molecular weight higher than 200,000 should be avoided as it is antigenic and ;may act as an anticoagulant. Other ligands that may be coupled to Factor VIII include polyhydric alcohols and alcohol polymers such as PEG or M-PEG (MW 500–5000) poly (N-vinylpyrrolidone), sialic acid (or glycopeptides containing exposed sialic acid such as fibrinogen degradation products or gamma-globulin degradation products) von Willebrand factor, human serum albumin, poly D+ alanine, or poly D+ glutamic acid or poly D+lysine and others. These ligands may be linked to FVIII .with cyanogen bromide, CDI, DST (dichloro-s-triazine), TST (trichloro-s-triazine) or MST (monochloro-s-triazine), bifunctional crosslinking reagents, n-hydroxysuccinimide gluataraldehyde or other reagents. However, the reaction conditions should be optimized for each ligand and each linking agent. For example, when cyanogen bromide was used under the following conditions, coupling FVIII to dextran was not uniform or consistent.

Two-percent ice-cold Dextran (MW 10, 40 and 70 KD) in 0.05M sodium carbonate buffer was brought to pH 10.0 with NaOH. The reaction mixture was stirred on ice in a fume hood. Solid CNBr was added to a final concentration of 0.5% w/v. The reaction was allowed to proceed for 1 hour with constant addition of NaOH to maintain the pH at about 10 (9.5–10.2). The dextran was dialyzed against several changes of distilled water. It was then brought into contact with Factor VIII as described above at a pH of 7.4 over night at 4° C. The Factor VIII activity showed evidence of coupling to the dextran with a similar (50%) recovery of the activity but the reproducibility of this method was so poor that only about 25% of the Factor VIII samples showed clear evidence of coupling. However, with a higher coupling reaction pH, [such as about 7.8 to about 9.0) reproducibility would be expected to improve, but the Factor VIII would be unstable (stability may be improved by subsequently lowering the pH; nevertheless, some of the activity would be lost during the high pH exposure). However, in light of the present description, optimization of each procedure is within the skill of the art.

It is to be noted further that PEG activated with TsT according to the method of Abuchowski, 1977, failed to couple to Factor VIII under the following conditions: Monomethoxypolyethylene glycol (MW 1900 and 5000) was activated by dissolving in benzene to a 5% concentration; 2% anhydrous sodium carbonate was added as a base; TsT was added to a concentration of 75 mM and reaction mixture was stirred overnight at room temperature. The solution was filtered to remove the carbonate and PEG was precipitated by the slow addition of petroleum ether to a final concentration of 60%. The precipitate was collected, resuspended in benzene and reprecipitated three times to remove all residual TsT. Optimum conditions for coupling TsT-PEG to Factor VIII were determined by using coupling to human serum albumin as a model (albeit human serum albumin is a poor model for Factor VIII). This test however, enabled the investigators to determine whether any coupling would occur within reaction conditions that might be suitable for FVIII and would not inactivate Factor VIII. Even under optimum coupling conditions for FVIII, 10–20% of the amino groups on HSA reacted with TsT-PEG. These conditions (pH 7.5, 2.0 hours at 4° C.) were applied to several preparations of Factor VIII concentrate (specific activity about 0.5 units/mg). The concentrates were diluted to 1.0 mg/ml in 0.3 M NaCl, 0.05 M hepes, pH 7.5 to prevent protein precipitation by the PEG. DsT-PEG was added at 10%. No measurable coupling occurred under these conditions. Additional experiments were performed with a partially purified Factor VIII preparation that had a specific activity of about 50 U/mg (e.g. eluate of the first PE-E5 chromatography described above). The DsT-PEG had to be reduced to 1% to prevent Factor VIII precipitation. Attempts to keep the Factor VIII in suspension with detergents such as Tween 80 and Triton X-100 did not improve coupling ability even at 2% DsT-PEG (higher DsT-PEG concentrations still caused precipitation). A lower molecular weight PEG may be expected to yield some coupling, but would probably be less effective in prolonging the disappearance-time and preventing an immune response. However, variations in the coupling procedure are expected to improve results.

Another preferred procedure employs activating PEG with trichloro-s-triazine; substituting another chloro group in the resulting dichloro-s-triazine (DsT-PEG) with aniline to form monochloro-s-triazine (MsT-PEG) and then coupling the protein essentially according to the procedure disclosed in U.S. Pat. No. 4,229,537. MsT is stable in aqueous solution, therefore, MsT may be used to couple Factor VIII to M-PEG or PEG in aqueous phase and the reaction may be allowed to proceed to equilibrium under very mild controlled conditions.

For example, 40 g of M-PEG (MW 2000) or PEG (MW 1450) may be dissolved in 100 ml of dioxane and the mixture brought to 50° ± 2° C. with stirring in an oil bath. N,N-diisopropylethylamine in dioxane will be added (20 ml, 2 M). After 30 minutes, 20 ml of 1 M recrystallized TsT in dioxane will be added. After 60 minutes at 50° C., the reaction mixture will be brought to room temperature or below by dilution in cold (5–10° C.) anhydrous heptane (or petroleum ether) and precipitated. The dilution/precipitation procedure will be repeated three times; the final precipitate (1 volume) will be dissolved in 100 ml of chloroform or 200 ml benzene-dioxane or benzene-acetone, reacted with two volumes of aniline in dioxane at room temperature for 30 minutes and reprecipitated three times with heptane or petroleum ether as above. The thus activated M-PEG or PEG can be dried in vacuo and stored at −80° C.

When used to modify Factor VIII, a 1–2% aqueous solution of the activated aniline-treated PEG will be incubated for 6–24 hours with partially purified or purified Factor VIII (activity higher than 0.2 units/mg) in 0.25 M CaCl$_2$ and 0.02 M MES or 0.05 M acetate buffer pH 6.0. The protein concentrations of the Factor VIII preparation should be at least 0.5 mg/ml. The reaction can be stopped by the addition of any suitable primary amine such as lysine (or another compound with an amino group such as ethanolamine or ammonium chloride or ammonium sulfate) and the conjugated Factor VIII may be separated from the reaction mixture by concentration and diafiltration using a Minitan apparatus, preferably in the presence of 0.5% albumin.

In general, the range of reaction conditions that do not cause Factor VIII inactivation (by precipitation or otherwise) are the following:

| | |
|---|---|
| pH | 5.8–7.8 |
| temperature | 30° C. and lower |
| ionic strength | 0.01 - preferably about 2.0 M (but can be higher) |
| PEG concentration | less than 5% |

In addition, the total protein concentration should be monitored to ensure that Factor VIII will couple preferentially and substantial amounts of contaminating protein will not form insoluble species.

Therefore, the coupling procedure must be operative under these conditions.

If PEG or M-PEG is to be used as a ligand, its molecular weight should be within the range of about 500–5000.

Albumin or possibly von Willebrand factor can be coupled to Factor VIII with glutaraldehyde, as has been done when albumin was coupled to uricase (Remy, M., and Pasnamsky, M.; Lancet 2:68–70, 1978); M-maleimidobenzoyl sulfosuccinamide ester (sulfo-MBS) or other cross-linking reagents may also be used. Similarly, sialic acid containing glycopeptides can be coupled to FVIII with glutaraldehyde or other reagents as has been the case with glutamine-asparaginase (Holcenberg, J.S. et al., *J. Biol. Chem.* 250:4165–4170, 1975; or poly (vinylpyrrolidone) can be activated by partial hydrolysis, the N-hydroxy succinimide ester formed and this could be coupled to FVIII as it was to human hexaminidase A (Geiger, B.W., et al., *Eur. J. Biochem.* 43:141–144, 1977). Alternatively, n-carboxy-DL-alanine anhydride might be used as it was with trypsin (Annon, R. and Neurath, H., *Immunochemistry,* 7:241–250, 1970).

The foregoing representative coupling procedures are applicable to all proteins having mammalian Factor VIII activity (such as human, porcine and bovine Factor VIII and fragments of these proteins whether such proteins and fragments are isolated from natural sources or synthesized, such as by recombinant techniques).

In vivo Disappearance Time of Factor VIII Conjugate

The in vivo disappearance time of native and modified Factor VIII was tested in a hemophilic dog (12.72 kg, estimated blood volume: 966 ml and plasma volume: 638 ml). Factor VIII for this experiment was purified to a specific activity of 980 units/mg under pyrogen-free conditions at an endotoxin level of less than 6 ng per 1000 units. The high purity FVIII was employed to insure performance of a well-controlled experiment with minimal contaminating protein, including von Willebrand Factor, and does not imply that the purity needs to be high. The Factor VIII was purified in accordance with the complete (PE-E5/affinity/PE-E5) chromatographic procedure outlined above and all buffers were prepared with sterile, pyrogen-free, distilled water. Half of the Factor VIII preparation was coupled to dextran T70 at a concentration of 1000 U/ml with a 52% loss in activity. Both samples were dialyzed against 0.1 M CaCl$_2$, 0.05 M sodium acetate, pH 6.2 and 10% HSA was added prior to dialysis to prevent non-specific adsorption of Factor VIII protein on the dialysis membrane. The dog was injected with 0.7 ml of acepromazine (tranquilizer) and 0.3 ml of Dimethane-10 (an antihistamine) 15 minutes prior to intravenous infusion of the Factor VIII. One ml of dextran-Factor VIII conjugate (activity 235 units) was diluted to 8 ml with sterile saline and infused intravenously at 1 ml/min. Three-ml blood samples were each drawn into 0.3 ml of 3.8% trisodium citrate anticoagulant both pre-infusion and post-infusion (after 0.25, 0.5, 1, 1.5, 3, 6, 12 and 24 hours).

One week later, the experiment was repeated with 438 units of unmodified Factor VIII as a control.

No adverse effects were observed with infusion of either Factor VIII or conjugate.

The hemoglobin, total protein and platelet count remained stable throughout the experiment. The white blood cell count fluctuated for the first three hours post-infusion but returned to pre-infusion levels by six hours. The Factor VIII coagulant activity was monitored for 24 hours post-infusion by both the two-stage and the one-stage assay. The results are shown in the Table below:

TABLE

FACTOR VIII ACTIVITY IN THE CIRCULATING BLOOD OF A HEMOPHILIC DOG AFTER INFUSION OF HUMAN UNMODIFIED OR DEXTRAN-COUPLED FACTOR VIII

| Time Post Infusion | Factor VIII[1,3] | | T 70 (ox)-Factor VIII[2,3] | |
|---|---|---|---|---|
| | O/S | T/S | O/S | T/S |
| 0 mins | 0.08 | 0.079 | 0.075 | 0.078 |
| 15 mins | 0.75 | 0.8 | 0.39 | 0.32 |
| 60 mins | 0.71 | 0.72 | 0.37 | 0.32 |
| 90 mins | 0.65 | 0.43 | 0.36 | 0.37 |
| 3 hours | 0.45 | 0.37 | 0.38 | 0.37 |
| 6 hours | 0.35 | 0.29 | 0.25 | 0.34 |
| 9 hours | 0.30 | ND | 0.28 | 0.27 |
| 12 hours | 0.23 | 0.19 | 0.27 | 0.24 |
| 24 hours | 0 | 0.10 | 0.16 | 0.16 |
| 48 hours | ND | ND | 0.05 | 0.04 |

[1]Human unmodified Factor VIII.
[2]Dextran-coupled Factor VIII.
[3]Factor VIII activity was assayed by the one-stage (O/S) and two-stage (T/S) methods against a human Factor VIII standard (WHO 3rd International Standard). It is set fourth in this table as units/ml. THe pre-infusion level of Factor VIII (0.08 u/ml) was subtracted from all post infusion samples.

The rate of clearance of conjugated and native Factor VIII is shown in FIG. 1. As indicated in Table I, the Factor VIII measurements with each of the one-stage and two-stage assay were comparable.

The data in FIG. 1 show that all of the infused (both conjugated and unconjugated) Factor VIII was recovered in the bloodstream. However, after five hours, only half of the infused unmodified factor remained in the bloodstream compared with 90% of the conjugate. In addition, the level of the conjugate did not decrease to 50% of its peak activity until 21 hours post-infusion. After 24 hours, more than 85% of the unmodified factor had been eliminated from the bloodstream whereas 43% of the infused conjugate remained. After 48 hours (data not shown) more than 10% of the conjugate remained in the circulating blood.

The period of rapid fall in the first three and one-half hours post-infusion accounted for about 50% of the FVIII injected in this and in other control experiments. This is significant because the absence of any fall in the level of the modified FVIII during this time compensated for losses in FVIII activity due to the modification procedure. Furthermore, the prolongation of the half-life in Phase II due to the infusion of the modified FVIII resulted in a major net increase in the effective disappearance time of the modified FVIII in vivo compared to the control. This, in turn, makes it possible to space FVIII infusions further apart or decrease the amount of the initial infusion. For example, since the conjugate has a longer disappearance time (as in FIG. 1) it would be possible to space consecutive infusions of Factor VIII at least 24 hours apart and maintain a continuous hemostatic blood level of 40% of the injected dose of the conjugate as opposed to 30% of the activity of unconjugated factor remaining after only 12 hours. This would result in a substantial saving of the Factor VIII that would otherwise be needed.

In addition, the conjugate had decreased antigenicity in vivo and decreased recognition of Factor VIII inhibition, as will be described below.

The activity of the conjugated Factor VIII was confirmed by conducting thrombin activation experiments with various dextran/Factor VIII conjugates in vitro. The conjugates showed comparable or higher activation rates (e.g. about 8-fold activation at 2-3 minutes from exposure to thrombin compared to 3.5-fold activation at 18-20 minutes for the unconjugated factor). In any event, the data show that the conjugates are thrombinactivatable and that conjugation does not impair and possibly enhances the ability of Factor VIII to act as a cofactor in Factor X activation.

Antigenicity of Conjugated Factor VIII

Antigenicity of Factor VIII was decreased by dextran conjugation of the Factor VIII.

Six female New Zealand white rabbits were immunized. Three were immunized with Factor VIII conjugates (coupled to dextran T 70) and three with non-conjugated Factor VIII by twice-weekly weekly intramuscular injections with 100 micrograms of the Factor VIII preparation in Freund's adjuvant (complete for the first injection and incomplete for the seven subsequent injections). Blood samples were taken after 2.5 weeks and after 4.5 weeks following the first injection. (One of the conjugate-immunized rabbits was excluded from the experiment because it did not complete the immunization protocol.) IgG from the samples was isolated by chromatography on DEAE-Affi-gel blue in accordance with the manufacturer's instructions and tested for Factor VIII inhibitor activity according to the method of Kasper, C., Throm. Diath. Haemorrh.. 33:640, 1975. Doubling dilutions were made in Hepes (n-2-hydroxyethylpiperazine-N'-2-ethanesulfonic acid) buffer, pH 7.35. A 0.1-ml antibody dilution aliquot was incubated at 4° C. overnight with 0.1 ml of normal plasma (buffer with normal plasma served as the control). Factor VIII assays were performed by the two-stage method and the inhibitor titer was expressed in Bethesda units/ml.

The results of the antibody titration for the five rabbits are shown in the Table, below.

TABLE

Formation of Human Antibodies to Factor VIII and to T 70 (ox)-Factor VIII Following Their Injection Into Rabbits

| ANIMAL | ANTIGEN | FACTOR VIII INHIBITOR TITER (Bethesda units/ml) |
|---|---|---|
| 018 | Factor VIII | 80 |
| 022 | Factor VIII | 48 |
| 025 | Factor VIII | 50 |
| 021 | T 70 (ox)-Factor VIII | 15 |
| 024 | T 70 (ox)-Factor VIII | 30 |

The above data show that all preparations caused the production of antibodies with the ability to inhibit Factor VIII activity. The conjugate-immunized rabbits had lower antibody titers. In an immunoprecipitation test, no antibodies to dextran were detected in any of the animals.

Interaction of Factor VIII Inhibitors With the Conjugate

Inhibitory activity of certain antibodies to Factor VIII was decreased by dextran-conjugated Factor VIII which indicates that the conjugate has decreased immunoreactivity (binding to antibody).

A total of 15 antibodies to Factor VIII were tested for their ability to neutralize the coagulant activity of unmodified Factor VIII and dextran-conjugated Factor VIII. Seven of these antibodies were monoclonal, seven were human polyclonal from Factor VIII inhibitor patients and one was a rabbit polyclonal antibody raised against high-purity Factor VIII. Monoclonal antibodies to Factor VIII can be purchased from Hybritech, Inc., San Diego, Calif., or Chemicon International, Los Angeles, Calif. or can be raised in accordance with techniques well-known in the art.

For polyclonal antibody titrations, IgG was purified from plasma by DEAE chromatography (dimethylaminoethyl Affi-Gel blue on Affi-Gel]as described above. For monoclonal antibodies, culture supernatants were titered without additional purification. For each antibody sample, doubling dilutions were made in 0.1 M NaCl, 0.05 Hepes, 0.1% HSA, pH 7.3. A 0.1-ml aliquot of each dilution was incubated with 0.1 ml of Factor VIII (activity: 1.0 units/ml) or conjugate (activity: 0.5 units/ml) for two hours at 37° C.

The amount of protein in both the unmodified and conjugated Factor VIII preparation was the same. Samples were assayed by the two-stage assay method. The amount of inhibition was determined as a percentage of the control (Factor VIII or conjugate incubated with buffer). The inhibitor titer was determined in Bethesda units/ml, i.e. the reciprocal of antibody dilution at which 50% inhibition is achieved in this assay system. The results are shown in Table III, below.

TABLE III

INHIBITOR TITERS FOR FACTOR VIII ANTIBODIES

| Antibody Source | Chain Specificity | Factor VIII Inhibitor Titer | T 70 (ox)-Factor VIII Inhibitor Titer |
|---|---|---|---|
| Monoclonals | | | |
| SNBTS 23.1 (G) | Heavy Chain | $10^4$ | 0 |
| SNBTS 98.1 | Not Detected | 2 | 2 |
| SNBTS 42.3 | Light Chain | 2 | 2 |
| SNBTS 83.1 (H) | Light Chain | 6 | 1 |
| SNBTS 78.1 | Light Chain | 4 | 4 |
| Chemicon | Light Chain | 4 | 4 |
| Hybritech (F) | Light Chain | 208 | 34 |
| Polyclonals | | | |
| NLS (A) | Light Chain | 133 | $33^4$ |
| TDH (B) | Light Chain | 250 | 100 |
| SLT | Light Chain | 700 | 710 |
| MRN (C) | Heavy Chain | 29 | 110 |
| GK 1824 | ND | 28 | 28 |
| GK 1825 (D) | ND | 90 | 40 |
| GK 1826 | ND | 75 | 75 |
| Rabbit (E) | ND | 100 | 55 |

[4] Maximum inhibition is less than 50% even with undiluted antibody so titer is taken as the lowest dilution giving maximum inhibition.

The above data show that of the 15 antibodies tested, 7 show decreased reactivity towards the conjugate as compared with unmodified Factor VIII. One antibody showed increased reactivity and seven antibodies showed no significant difference in reactivity. The results for antibodies designated A-H are depicted in graph form in FIG. 2.

One of the antibodies (known to be specific for the heavy chain of FActor VIII, i.e. the 90–210 kd peptide from the $A_1$-$A_2$-B region of the molecule) showed almost no inhibitory activity towards the conjugate (FIG. 2C) whereas another antibody (a spontaneously occurring antibody from a Factor VIII-inhibitor patient with specificity towards the same region of the Factor VIII molecule) showed increased reactivity towards the conjugate. This suggests that dextran coupling may alter the conformation of the heavy chain.

Of the remaining 13 antibodies, 8 were known to be specific for the light chain ($A_3$-$C_1$-$C_2$) region of Factor VIII and 5 were unclassified.

Six of these antibodies (two monoclonals, three polyclonals from inhibitor patients and one heterologous polyclonal from a rabbit) also showed decreased reactivity to the conjugate. Three of these light-chain-specific antibodies (from inhibitor patients) exhibit a plateau of maximum inhibition of the conjugate which is below the inhibition of unmodified Factor VIII (FIG. 2A, 2B, 2F). The implication of this finding is that patients with this type of inhibitor would benefit from treatment with conjugate. (Natural inhibitors to the heavy chain of Factor VIII are rarely found in patients treated with Factor VIII concentrates.)

The remaining seven antibodies tested did not show a change in inhibition ability towards the conjugate.

Treatment of Hemophilia

The standard treatment for hemophilia is infusion of Factor VIII (preferably in the form of Factor VIII concentrate) calculated on the basis that, in humans, half of the Factor VIII activity infused remains after 8-12 hours so that repeated infusions are usually required until the bleeding has stopped for 24–48 hours. Thus, infusions are usually given every 8 to 12 hours. The amount of Factor VIII to be infused in a patient every 8–12 hours depends on the extent of the deficiency of Factor VIII activity in that patient and on the severity of the bleeding episode or injury (Levine, P.H., in *Haemostasis and Thrombosis*, pp. 97–111; R.W. Colman et al., Editors, J.B. Lippincott, Philadelphia, U.S.A., 1987).

Thus, a 50 kg man: (a) with a spontaneous bleed would be treated with about 15 U/kg (750 U) to reach a maximum blood level of 30%, 2 × daily for 1-2 days; (b) with minor surgery or severe trauma would receive about 25 U/kg (1250 U) to reach a maximum blood level of 50%, 2 × daily for several days or longer; and (c) with major trauma or surgery about 40–50 U/kg (2000-2500 U) to reach a maximum level of 80–100%, 2–3 × daily for several days or weeks.

The amount of Factor VIII may be calculated from the fact that 1 unit of Factor VIII per kilogram of body weight elevates the bloodstream level about 2% (0.02 units) of the patient's usual Factor VIII level.

In the present invention, the amounts of infused Factor VIII required and the infusion frequency may be decreased by a factor calculated on the basis of: (a) the activity of the conjugate; (b) the absence (or decreased duration) of Phase 1, i.e. the absence of a period of rapid decrease in the blood level of Factor VIII after infusion; and (c) the virtual doubling (or other prolongation) of the half-life in Phase 2.

Appendix of Materials Sources

Dextran T-10, T 40 and T 70 and Sephadex G 25 were from Pharmacia Fine Chemicals, Division of Pharmacia, Inc., Piscataway, NJ. Affi-Gel-10, DEAE Affi Gel Blue, Coomassie Brilliant Blue G-250 and R-250 and gelatin were products of Bio Rad Laboratories, Richmond, Calif. Alkaline phosphatase conjugated goat anti-human IgG for Western Blots was obtained from Northeast Biomedical Laboratories, So. Windham, Me.

Monomethoxy polyethylene glycol, polyethylene glycol, heparin, Trasylol, sucrose and biuret reagent were purchased from Sigma Chemical Company, St. Louis, Mo. Cyanogen bromide, trichloro-s-triazine (TsT) dichloro-s-triazine (DsT), 1,1'carbonyldiimidazole and benzamidine hydrochloride were from Aldrich Chemical Co., Milwaukee, Wisc. Sodium periodate, sodium borohydride, were products of Fisher Scientific, Springfield, N.J. Aluminum hydroxide was from Superfos Biosector a/s, Copenhagen, Denmark; 2,4,6 Trinitrobenzene sulphonic acid was from Eastman Kodak Co., Rochester, N.Y. (pAmidinophenyl)-methanesulphonyl fluoride was obtained from California Medicinal Fine Chemical Corp., San Francisco, Calif.; and inhibitor 805 (Mitsubishi Chemical Co., New York, N.Y.).

Polyelectrolytes PE-E5 and PE-E100 were supplied by Monsanto Company, St. Louis, Mo.

Hemophilic plasma was purchased from George King Biomedical Co., Inc., Overland Park, Kans. Monoclonal antibodies to Factor VIII were purchased from Hybritech, Inc., San Diego, Calif.; and Chemicon International, Los Angeles, Calif.

All other buffers and inorganic salts were of the highest quality grade available. All buffers were prepared in water subjected to reverse osmosis and deionization. Where appropriate, sterile, pyrogen-free water was used.

All cited literature, patent applications, and patents are incorporated by reference in their entirety.

The present invention has been described in detail by reference to preferred embodiments. It will be obvious to those of ordinary skill in the art, however, that many variations (omissions, additions and modifications) are possible without departure from the scope of the claims.

We claim:

1. An infusible conjugate comprising a protein having Factor VIII activity covalently linked to a nonantigenic ligand, said conjugate:
    being activatable by thrombin;
    retaining at least a substantial portion of the activity of said protein prior to conjugation; and
    having a sufficiently prolonged in vivo disappearance time compared to said protein in the unconjugated state to at least compensate for any loss of activity of said conjugate compared to said unconjugated protein.

2. The conjugate of claim 1 wherein said ligand is selected from the group consisting of polysaccharides, sialic acid, albumin, von Willebrand factor, glycopeptides containing sialic acid available for coupling, polyethylene glycols wherein said ethylene is substituted or unsubstituted, poly(vinylpyrrolidone), poly D+ alanine, poly D+ glutamine and poly D+lysine.

3. The conjugate of claim 1 wherein said ligand is a polysaccharide.

4. The conjugate of claim 3 wherein said ligand is dextran.

5. The conjugate of claim 1 wherein said protein is selected from the group consisting of native and recombinant mammalian Factor VIII.

6. The conjugate of claim 1 wherein said ligand is a substituted or unsubstituted polyethylene glycol.

7. The conjugate of claim 1 wherein said conjugate is formed using a member selected from the group consisting of trichloro-s-triazine, dichloro-s-triazine, monochloro-s-triazine, 1,1'carboaryldiimidazole, hydroxysuccinimide, monofunctional or bi-functional crosslinking agents, cyanogen bromide and sodium periodate, as the linking agent between said protein and said ligand.

8. The conjugate of claim 7 wherein said linking agent is sodium periodate and said ligand is nonantigenic, nonanticoagulant dextran.

9. The conjugate of claim 8 wherein said protein is selected from the group of manmmalian native and recombinant human antihemophilic factor and fragments thereof having antihemophilic factor activity.

10. The conjugate of claim 1 wherein said protein has been purified from a partially purified preparation of said protein by column chromatography using a positively charged ionic group on a solid-phase support as the adsorbent and a loading and washing buffer containing 0.05–2.0 M of a carbohydrate selected from the group consisting of glucose, sorbitol and lactose.

* * * * *